(12) United States Patent
Ho et al.

(10) Patent No.: US 6,388,756 B1
(45) Date of Patent: May 14, 2002

(54) OPTICAL METHOD OF MEASURING TRENCH DEPTH

(75) Inventors: Jau-Hwang Ho, Hsinchu Hsien; Osbert Cheng, Hsinchu, both of (TW)

(73) Assignee: United Microelectronics Corp., Hsinchu (TW)

( * ) Notice: Subject to any disclaimer, the term of this patent is extended or adjusted under 35 U.S.C. 154(b) by 0 days.

(21) Appl. No.: 09/396,995

(22) Filed: Sep. 15, 1999

(51) Int. Cl.[7] .......................... G01N 21/47; G01B 11/06
(52) U.S. Cl. ......................................... 356/626; 356/446
(58) Field of Search .............................. 356/446, 626, 356/73, 445, 448, 630, 632

(56) References Cited

U.S. PATENT DOCUMENTS 5,087,121 A * 2/1992 Kakuchi et al. .............. 356/73
5,807,761 A * 9/1998 Coronel et al. ............... 438/14
6,275,297 B1 * 8/2001 Zalicki ........................ 356/496

* cited by examiner

Primary Examiner—F. L. Evans
Assistant Examiner—Layla Lauchman

(57) ABSTRACT

An optical method for measuring a trench depth, applicable to a substrate having a trench therein, wherein the substrate has a first surface, and the trench has a bottom surface to serve as a second surface as well as a depth. The method involves measuring a total reflectance from the substrate using different wavelengths, wherein the total reflectance is determined by a first actual reflectance from the first surface, a second actual reflectance from the second surface, and a scattering factor. The second actual reflectance is then determined from the measurement of the first actual reflectance from the first surface and the calculation result of the scattering factor. Since a trench depth is determined from the second actual reflectance, the trench depth is calculated after acquiring the second actual reflectance.

9 Claims, 3 Drawing Sheets

OPTICAL METHOD OF MEASURING TRENCH DEPTH

BACKGROUND OF THE INVENTION

1. Field of Invention

The present invention relates to a method for measuring a silicon trench depth. More particularly, the present invention relates to a method for measuring the silicon trench depth using optics.

2. Description of Related Art

Depth measurement in a semiconductor process involving probing the substrate surface. Since the depth of a trench or an opening is measured according to the surface fluctuation of the substrate, the method is typically a contact-type measurement. If the surroundings interfere with a test probe during depth detection, the resulting measurements may be inaccurate, so a stress is usually applied to the test probe to prevent the probe from drifting. This adds a loading to the probe so as to allow easy measurement. However, such stress causes damage, as well as cuts, on the substrate surface. Furthermore, the stress leads to electrical problems such as bridging or leakage current. As a result, the reliability of the device is reduced.

As the size of the probe is not reduced without limitation, the probe is easily stuck in the trench during measurement when a very narrow trench, such as the trench with an opening width of the below 1 μm, is measured. Since the probe has a lower measurement rate, it is unable to perform a great deal of tests. In addition, there may be errors for the measurement accuracy, which reduces the resolution when the substrate is less smooth.

SUMMARY OF THE INVENTION

The invention provides an optical method for measuring a trench depth, where a non-destructive measurement is performed on a substrate to improve the reliability of a device.

It is therefore an object of the invention to provide an optical method, which method allows measurement of a narrower trench and provides a higher measuring rate, so that operation time is saved while resolution is improved.

As embodied and broadly described herein, the invention provides an optical method for measuring the trench depth, applicable to a substrate having a trench, wherein the substrate has a first surface, and the trench has a bottom surface to serve as a second surface as well as a depth. The method involves measuring a total reflectance (R) from the substrate using different wavelengths, wherein R is determined by a first actual reflectance from the first surface, a second actual reflectance from the second surface, and a scattering factor (ΔR). The second actual reflectance is then determined from the measurement of the first actual reflectance from the first surface and the calculation result of ΔR. Since a trench depth d is determined from the second actual reflectance, d is calculated after acquiring the second actual reflectance.

The first actual reflectance in this case is determined from a first reflectance $R_1$ and a first area factor α, whereas the second actual reflectance is determined from a second reflectance $R_2$ and a second area factor β.

According to the present invention, the optical method for measuring the trench depth not only allows measurement of the narrower trench, but also provides a higher measuring rate. Furthermore, since the optical method provides non-destructive measurement, the reliability of the device increases.

It is to be understood that both the foregoing general description and the following detailed description are exemplary, and are intended to provide further, explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

The invention measures the reflectance for the substrate surface using light of different wavelengths, while the trench depth to be measured is calculated from a model for reflectance. The invention thus provides optical measurements for the trench depth in the semiconductor structure. Since the optical measurement is a non-destructive measurement, no damage is done to the substrate surface after the measurement. The invention is also applicable to measuring a narrower trench and provides a higher measuring rate, thus saving operation time.

Figure 1:
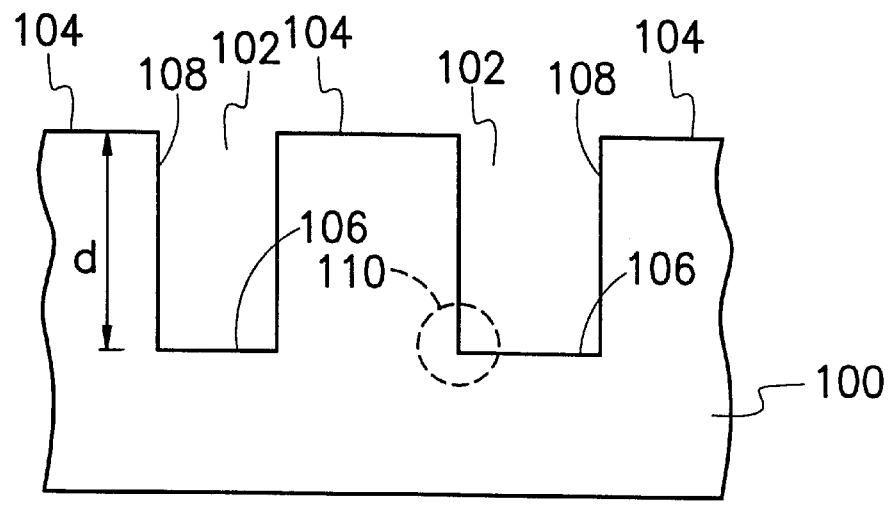
FIG. 1 is a schematic, cross-sectional diagram illustrating a substrate having a trench.

Referring to FIG. 1, which is a schematic, cross-sectional diagram illustrating a substrate 100 having a trench 102, wherein d is the trench depth to be measured. The substrate 100 has two main surfaces, with a first surface 104 being the surface of the substrate 100 and a second surface 106 being the bottom surface of the trench 102, while both surfaces may serve to reflect light. As the first surface 104 and the second surface 106 are at different heights, an optical path difference may occur when the apparatus for measuring the reflectance projects light on the substrate 100. As a result, the signal detected by the apparatus is the light interference after reflecting from the first surface 104 and the second surface 106, while the signal obtained is the total reflectance (R) from the whole surface of the substrate 100.

Since d of the trench 102 is related to R from the substrate 100, d of the trench 102 is calculated with reference to equation (1) as follows:

$$R = \alpha \times R_1 + \beta \times R_2 + \Delta R \tag{1}$$

where R is obtained from the combined interference of the actual reflected light from the first surface 104 and the second surface 106. As $R_1$ and $R_2$ are reflectances measured from the first and the second surfaces 104 and 106, respectively, the first actual reflectance and the second actual reflectance are represented by $\alpha \times R_1$ and $\beta \times R_2$. From equation (1) above, α is an area factor of the first surface 104 out of the substrate 100, β is an area factor of the second surface 106 out of the substrate 100, and ΔR is a scattering factor added for error compensation after the actual reflected light from the first surface 104 and the second surface 106 are calculated, as light scattering and light diffraction may occur during the actual measurement.

$R_1$ is obtained solely from the reflection strength after projecting light on the substrate 100, while the $R_2$ is determined from the depth d of the trench 102 as well as the refraction rate and the penetration rate (decay rate) of the medium in the trench 102. $\alpha$ and $\beta$ are estimated from the design of the layout when the trench 102 is larger. In contrast, a larger error is estimated when the trench 102 becomes smaller, so a more accurate value is obtained via calculation.

Figure 2:
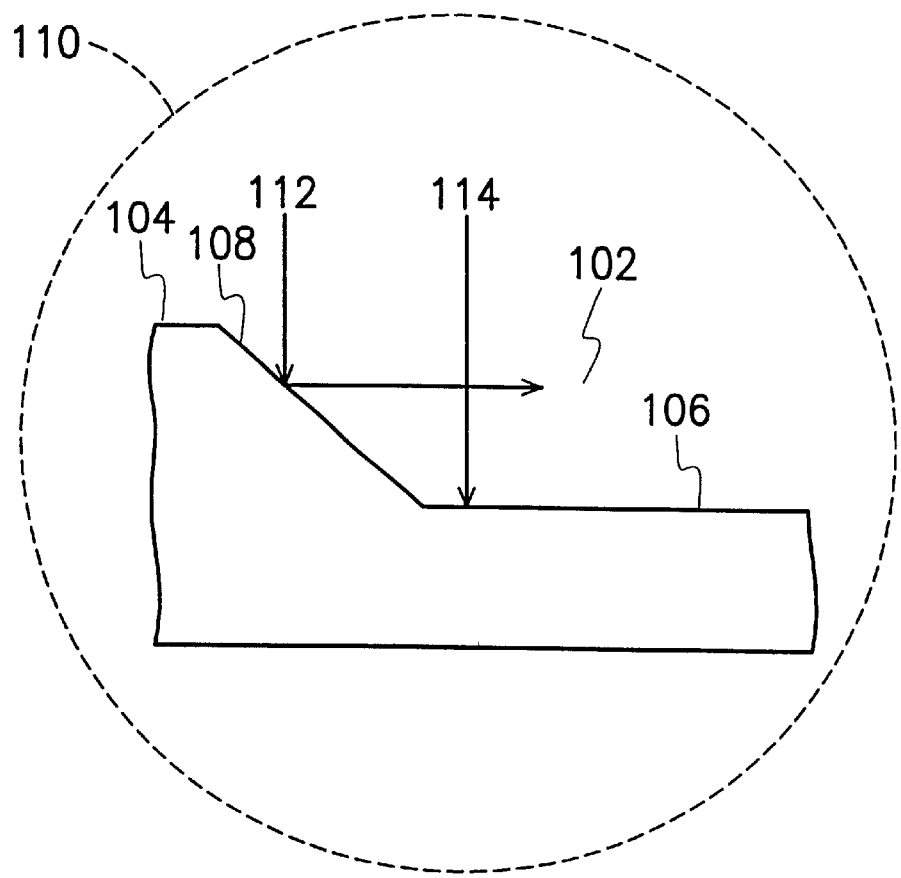
FIG. 2 is an enlargement of a bottom corner of the trench in FIG. 1.

Since $\Delta R$ approaches zero when the trench 102 becomes larger, it is not considered in equation (1) as it does not influence the calculation result. However, the gradient of the sidewall 108 of the trench 102 may seriously influence the measured reflectance when the trench is very small. FIG. 2 is an enlargement of a bottom corner of the trench 102 in FIG. 1. The sidewall 108 of the trench 102 reflects the incident light 112, which interferes with the light 114 projecting onto the bottom of the trench 102. As a result, the sidewall 108 of the trench 102 becomes one reflecting source other than the surface 104 of the substrate 100 and the surface 106 of the trench 102. As the reflecting source is the light measured during light scattering and interference, it is necessary to add $\Delta R$ when estimating R from the substrate 100.

Figure 3:
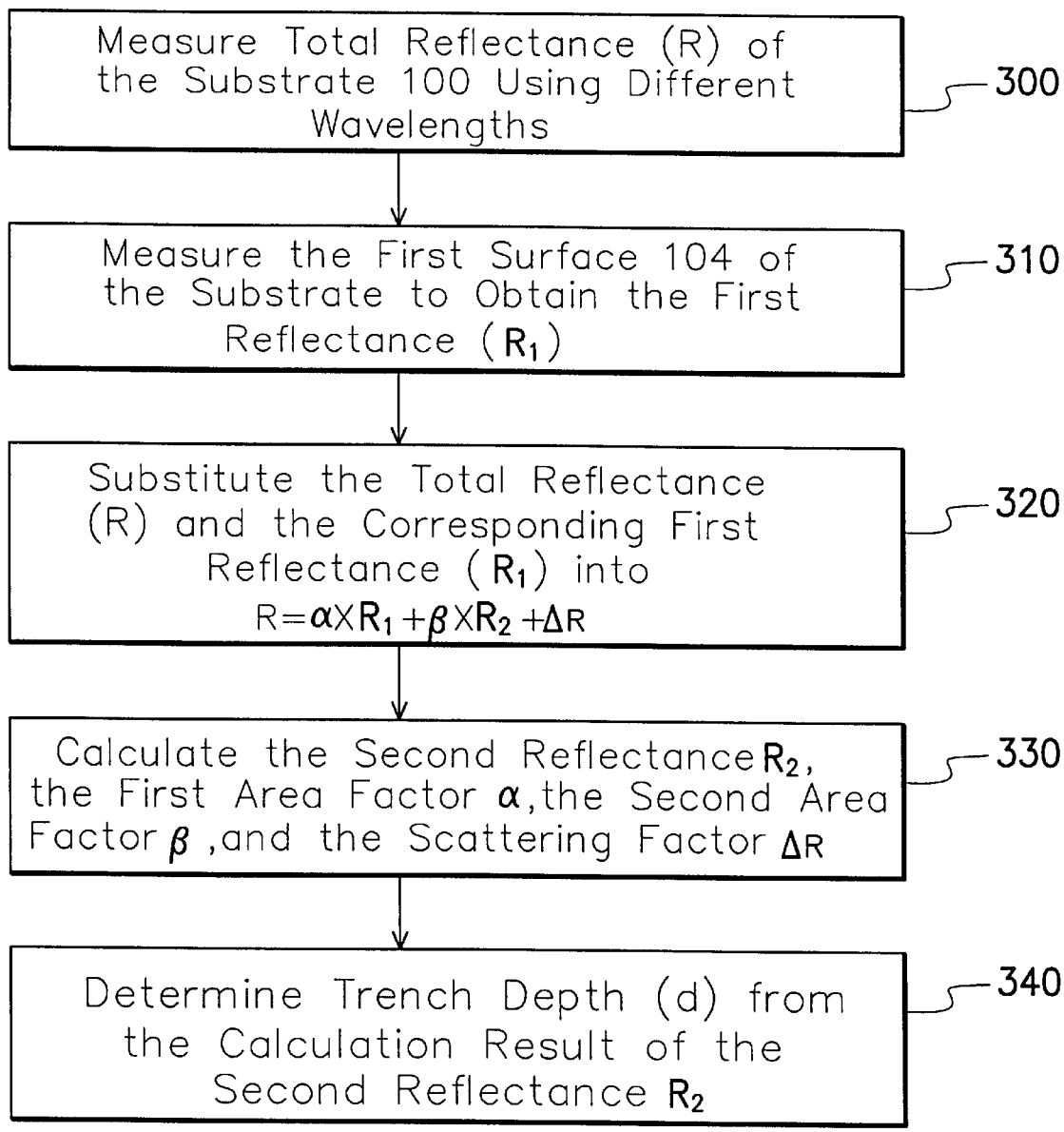
FIG. 3 is a flow chart of steps in the optical method for measuring the trench depth according to the preferred embodiment of the invention.

The steps for measuring the trench depth are described in the invention with reference to FIG. 3. A wavelength range of about 260–750 nm is selected in the invention. First of all, a light source of different wavelengths with spot size larger than 10 $\mu$m is projected onto the surface of the substrate 100 in order to measure the R (step 300). With the R serving as a transverse axis and wavelength as a longitudinal axis, a graph showing the relation between the R and the wavelength is drawn. The reflection strength from the surface 104 of the substrate 100 is measured using different wavelengths, so that a first reflectance $R_1$ is obtained (step 310). Since a second reflectance $R_2$ is a function of the depth d of the trench 102, the substitution of R and the corresponding $R_1$ into equation $R=\alpha \times R_1+\beta \times R_2+\Delta R$ (step 320), together with comparison to the measured experimental value of R, result in an area factor $\alpha$ covered by the first surface 104, an area factor $\beta$ covered by the second surface 106 (step 330), $\Delta R$, and d (step 340) to be calculated.

Figure 4:
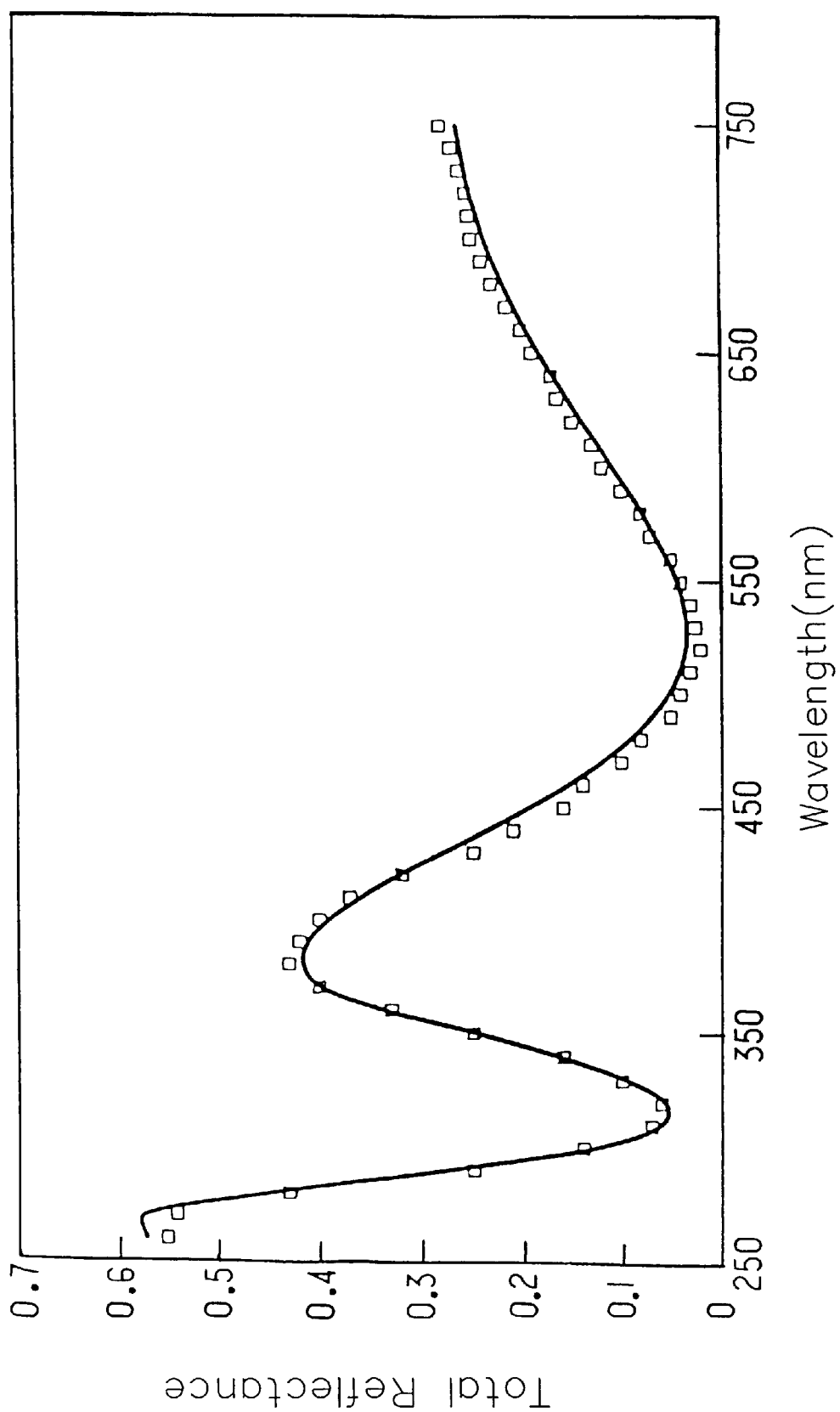
FIG. 4 is a graph showing the result of total reflectance measured at different wavelengths according to the preferred embodiment of the invention.

FIG. 4 is a graph showing the result of R (represented by □ in the graph) measured at different wavelengths as well as the result calculated from equation (1) above (represented by a curve in the graph). From equation (1), the area factor $\alpha$ calculated from the first surface 104 is 0.3, the area factor $\beta$ from the second surface 106 is 0.6, and the trench depth d is about 3950 angstroms. For comparison, the trench depth measured by scanning electron microscope (SEM) is about 3960 angstroms. This shows that the preferred embodiment of the invention is certainly applicable to measuring the trench depth.

The optical method disclosed in the invention not only measures a narrower trench, but also provides a higher measuring rate. Thus, this saves operation time.

In addition, the substrate surface is not damaged when measurement is made using an optical method.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An optical method for measuring a silicon trench depth, applicable to a substrate having a trench therein, wherein the substrate has a first surface, and the trench has a bottom surface to serve as a second surface as well as a depth, the method comprising steps of:

measuring a total reflectance (R) from the substrate using different wavelengths, wherein R is determined by a first actual reflectance from the first surface, a second actual reflectance from the second surface, and a scattering factor;

measuring the first actual reflectance from the first surface using different wavelengths;

calculating the scattering factor;

calculating the second actual reflectance from results of the first actual reflectance and the scattering factor; and determining the depth from the calculation result of the second actual reflectance.

2. The optical measuring method of claim 1, wherein the first actual reflectance is determined from a first reflectance and a first area factor of the first surface.

3. The optical measuring method of claim 2, wherein the first area factor is an area ratio of the first surface to a total area of the substrate.

4. The optical measuring method of claim 2, wherein the first actual reflectance is obtained by measuring reflectance from the first surface.

5. The optical measuring method of claim 1, wherein the second actual reflectance is determined from a second reflectance and a second area factor of the second surface.

6. The optical measuring method of claim 5, wherein the second area factor is an area ratio of the second surface to total area of the substrate.

7. The optical measuring method of claim 1, wherein the R of the substrate is measured in a wavelength range about 260–750 nm.

8. A method for measuring a trench depth using optics, applicable to a substrate having a trench therein, wherein the substrate has a first surface, and the trench has a bottom surface to serve as a second surface as well as a depth, the method comprising steps of:

measuring a total reflectance from the substrate using different wavelengths;

measuring a first reflectance from the first surface using different wavelengths, wherein the total reflectance from the substrate is determined from a first actual reflectance from the first surface, a second actual reflectance from the second surface, and a scattering factor, wherein the first reflectance and a first area factor are directly proportional to the first actual reflectance, a second reflectance and a second area factor are directly proportional to the first actual reflectance, and the depth is determined from the second reflectance; and calculating the first area factor, the second area factor, the scattering factor, and the trench depth from results of the total reflectance and the corresponding first reflectance.

9. The measuring method of claim 8, wherein the total reflectance of the substrate is measured in a wavelength range about 260–750 nm.

* * * * *